United States Patent [19]
Jones et al.

[11] Patent Number: 4,784,606
[45] Date of Patent: Nov. 15, 1988

[54] ORTHODONTIC BRACKETS MADE FROM ION EXCHANGE STRENGTHENED GLASS

[75] Inventors: Robin M. F. Jones, Pennington; Carl Panzera, Belle Mead; Robert D. DeLuca, Pennington, all of N.J.

[73] Assignee: Johnson & Johnson Consumer Products, Inc., New Brunswick, N.J.

[21] Appl. No.: 36,640

[22] Filed: Apr. 10, 1987

Related U.S. Application Data

[63] Continuation-in-part of Ser. No. 932,745, Nov. 19, 1986, and a continuation-in-part of Ser. No. 921,984, Oct. 22, 1986, abandoned.

[51] Int. Cl.⁴ .............................................. A61C 3/00
[52] U.S. Cl. .......................................... 433/8; 433/9; 501/7
[58] Field of Search ............................ 433/9, 8, 10, 24; 501/7

[56] References Cited

U.S. PATENT DOCUMENTS

| | | | |
|---|---|---|---|
| 3,428,513 | 2/1969 | Denman | 501/7 |
| 3,573,020 | 3/1971 | Karstetter | 501/7 |
| 4,074,992 | 2/1978 | Voss | 501/7 |
| 4,189,325 | 2/1980 | Barrett et al. | 501/7 |
| 4,216,583 | 8/1980 | Reynolds | 433/9 |
| 4,595,598 | 6/1986 | DeLuca et al. | 433/9 |

Primary Examiner—John J. Wilson
Attorney, Agent, or Firm—Charles J. Metz

[57] ABSTRACT

Orthodontic brackets are made from ion exchange strengthened glass. In a preferred embodiment, the glass is a lithium alumino silicate srengthened with sodium ions.

4 Claims, 7 Drawing Sheets

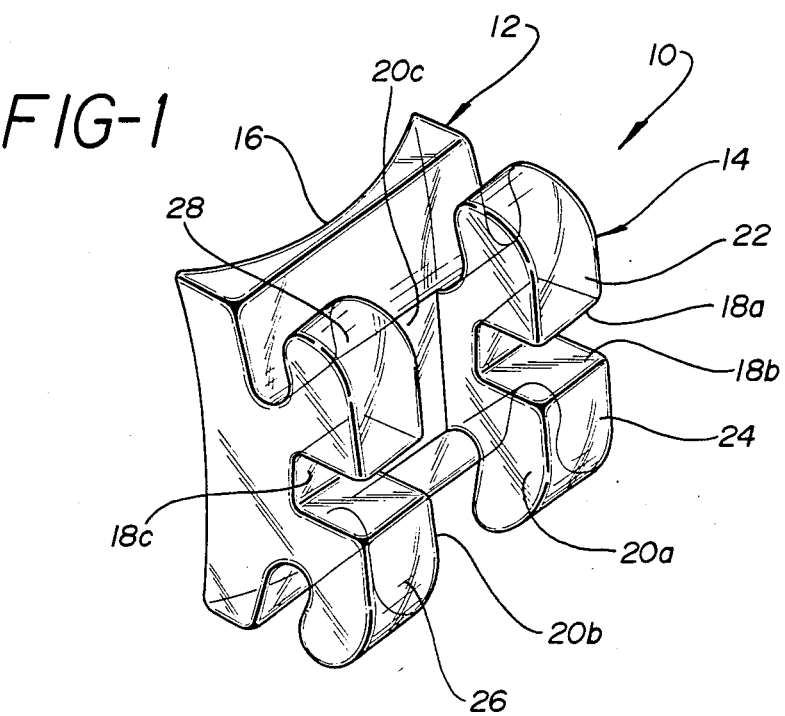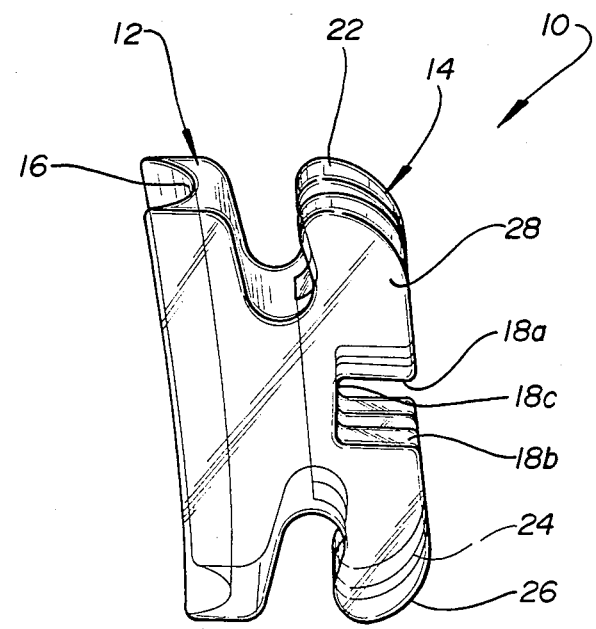

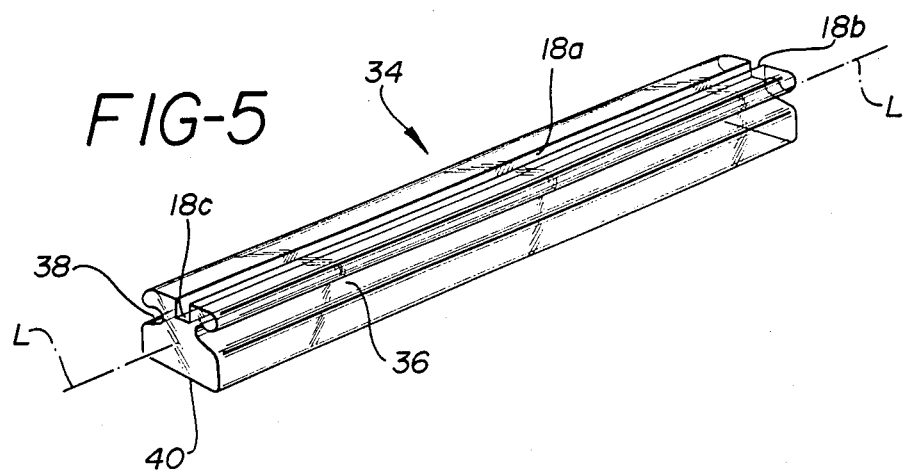
FIG-5
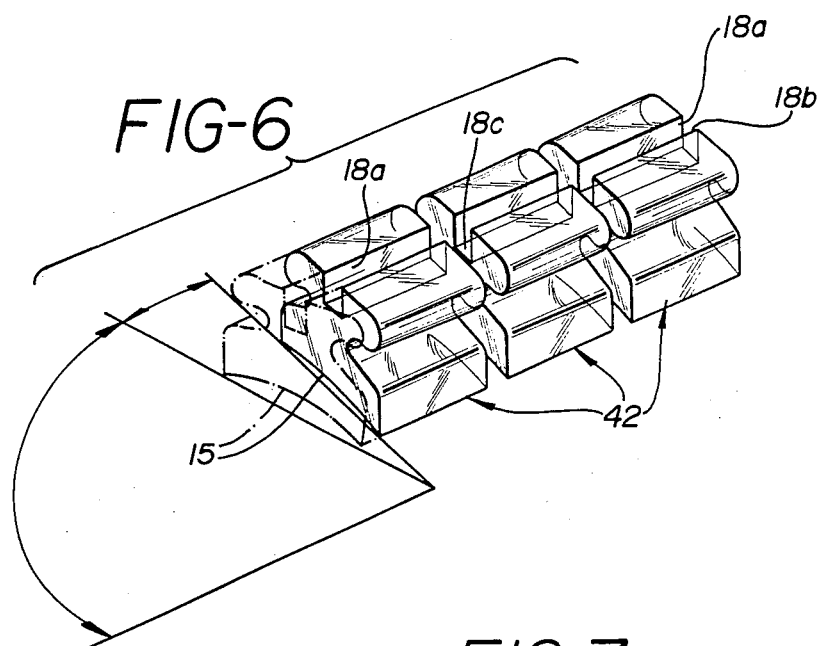
FIG-6
FIG-7
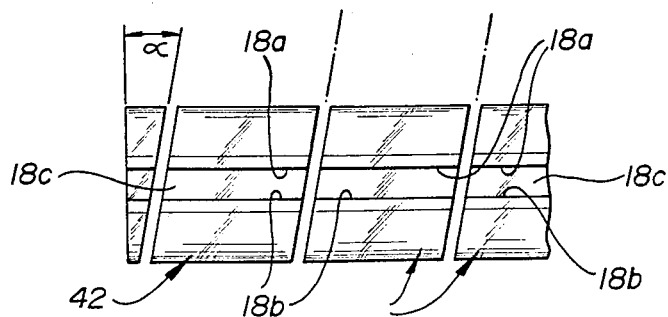

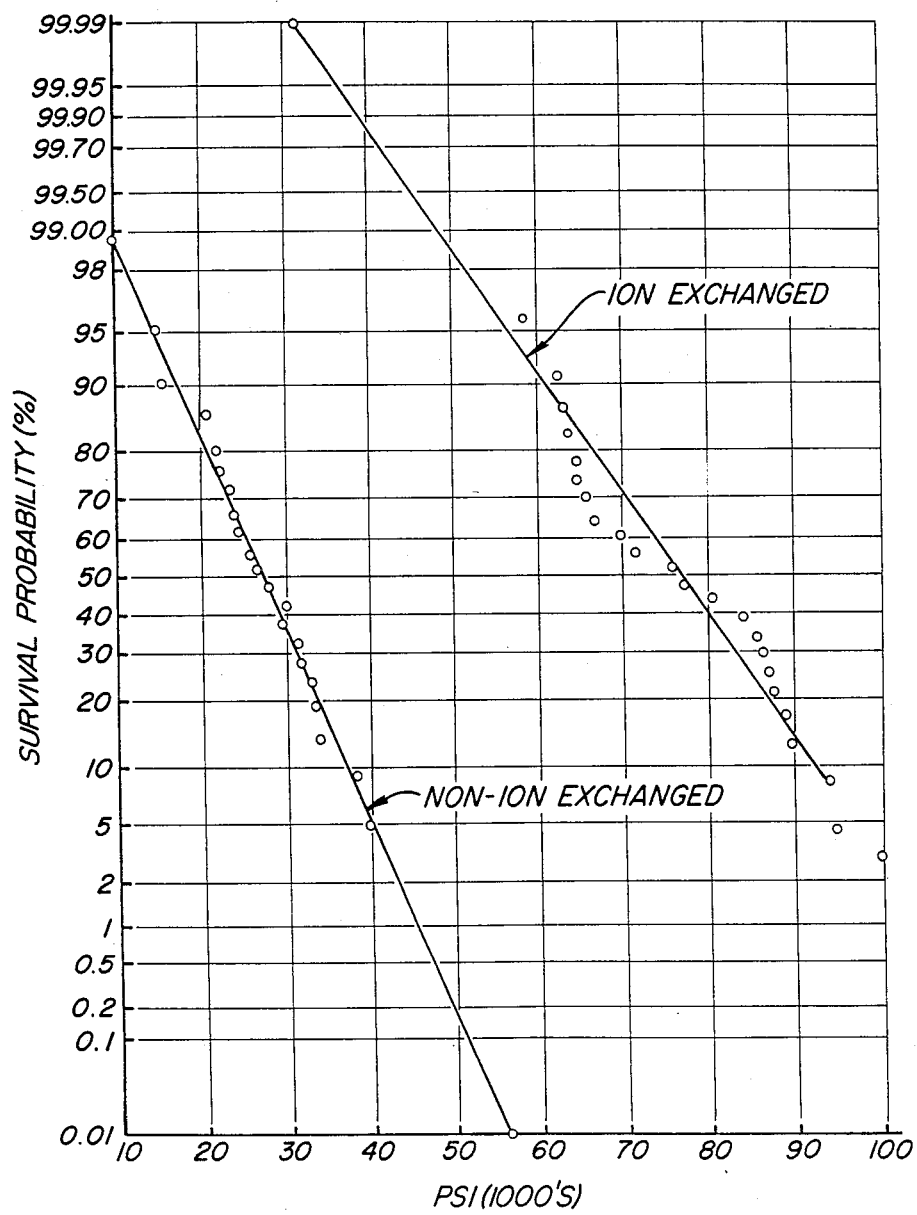

ORTHODONTIC BRACKETS MADE FROM ION EXCHANGE STRENGTHENED GLASS

This application is a continuation-in-part of our application Ser. No. 932,745, filed Nov. 19, 1986, and our application Ser. No. 921,984, filed on Oct. 22, 1986, and now abandoned.

The invention relates to orthodontic brackets made from ion exchange strengthened glass.

BACKGROUND OF THE INVENTION

Orthodontic brackets attach directly to teeth and serve to transmit corrective forces from an orthodontic archwire to the tooth to which the bracket is attached. The requirements for an orthodontic bracket are quite severe. First, it must have sufficient mechanical strength to withstand the forces to which it will be subjected, including the forces transmitted by an archwire, ligation forces, and mastication forces. Second, it must be chemically inert in the oral environment so that it will not corrode and will be and remain biologically inert. The bracket must meet these requirements, and still remain small enough to fit on the tooth. Despite proposals for making orthodontic brackets from many different materials, the overwhelming majority of orthodontic brackets in use today are made of metal, usually stainless steel. Metal brackets meet all of the essential requirements, but they have one undesirable attribute—they are unsightly. A person undergoing orthodontic treatment has a conspicuous amount of metal in full view on the front surfaces of his or her teeth. And since the treatment may extend over a number of years, this unsightly appearance must be endured for a considerable period of time.

The incentive to make brackets from less unsightly materials has existed for many years. But recently, orthodontic treatment has been given to increasing numbers of adults, for whom the unsightly appearance of metal brackets is more than a mere annoyance. Therefore, the incentive to provide more esthetic orthodontic treatment is even greater now than it has ever been.

To avoid the unsightly appearance of metal orthodontic brackets, it is possible in some (but not all) cases to install the brackets and archwire on the lingual (tongue) side of the teeth. However, the lingual side technique usually takes longer and is usually more expensive than the customary buccal side technique to complete the treatment. Also, the brackets and archwire sometimes interfere with the tongue during speech. It has been proposed to make orthodontic brackets out of less unsightly material, such as transparent or translucent plastic (e.g., polycarbonate), or ceramic materials which more closely resemble natural dentition. A problem with both plastic materials and ceramics is that their mechanical strengths are borderline, and bracket breakage or creep can be a significant problem with them. The ceramic brackets that are currently in use are rather bulky (to overcome the physical property limitations of the material), so they tend to be somewhat uncomfortable to the patient. From an esthetic viewpoint, neither plastic nor ceramic materials are fully satisfactory either, because plastic may discolor (from coffee, tea, tobacco, and various foods), and the color of ceramic rarely exactly matches natural dentition. In an effort to overcome the strength limitations of ceramic and plastic brackets, it has been proposed to reinforce such plastic brackets with metal inserts or metal liners (for the archwire grooves). While this may help (although it will not completely alleviate) the strength limitations of plastic or ceramic brackets, such solutions bring back, to a least a limited degree, the esthetic problem for which the plastic or ceramic bracket was the proposed solution. Thus, to date, there are no commercially available orthodontic brackets that satisfactorily solve the above-described esthetic problem.

It has been proposed by the inventors herein to make orthodontic brackets from single crystal alumina (sapphire). For instance, see U.S. patent application Ser. No. 743,851, filed June 12, 1985, now U.S. Pat. No. 4,639,218. Such sapphire brackets are an excellent solution to the esthetic problem, but they are rather expensive and are not yet commercially available.

BRIEF SUMMARY OF THE INVENTION

The invention provides an orthodontic bracket comprising a base member for attaching to a tooth and a body member extending from the base member. The body member includes walls that define an archwire groove. The bracket of the invention comprises a glass that has been strengthened by ion exchange. The transparency characteristics of glass permit the provision of brackets that are much more esthetic than metal brackets. The ion exchange strengthening provides brackets that are stronger than the plastic or ceramic brackets that have heretofore been proposed.

THE PRIOR ART

Ion exchange has been used for some time to strengthen glass articles. For instance, see the following United States patents:
Grego et al., No 3,751,238
Mochel No. 3,790,430
Nakagawa et al., No. 3,959,000
Forker, Jr. et al., No. 4,483,700

The following patents disclose earlier attempts to provide esthetic orthodontic brackets:
Reynolds, U.S. Pat. Nos. 4,216,583 and 4,322,206 and Wallshein, U.S. Pat. No. 4,219,617, disclose orthodontic brackets made from injection molded, randomly oriented, polycrystalline ceramic materials. The brackets disclosed by Reynolds are commercially available, but they have not been a great commercial success.

Plastic orthodontic brackets containing metal reinforcement or liners for the archwire grooves are disclosed by Andrews in U.S. Pat. No. 3,930,311, by Stahl, U.S. Pat. No. 3,964,165, by Kurz, U.S. Pat. No. 4,107,844, By Frantz, in U.S. Pat. No. 4,299,569, and by Wallshein in U.S. Pat. No. 4,302,532.

BRIEF DESCRIPTION OF THE DRAWINGS

FIG. 1 is a perspective view of an orthodontic bracket made of ion-exchange strengthened glass;

FIG. 2 is a left side elevational view of the bracket of FIG. 1;

FIG. 5 is a perspective view of a glass rod from which orthodontic brackets of the invention can be produced;

FIG. 6 is a perspective view of a series of bracket blanks cut from the rod of FIG. 5;

FIG. 7 is a top plan view of the blanks of FIG. 6;

FIG. 9 is a graph of Survival Probability vs. flexural strength for glass control and ion exchanged glass flexural bars;

DETAILED DESCRIPTION OF THE INVENTION

Figure 3:
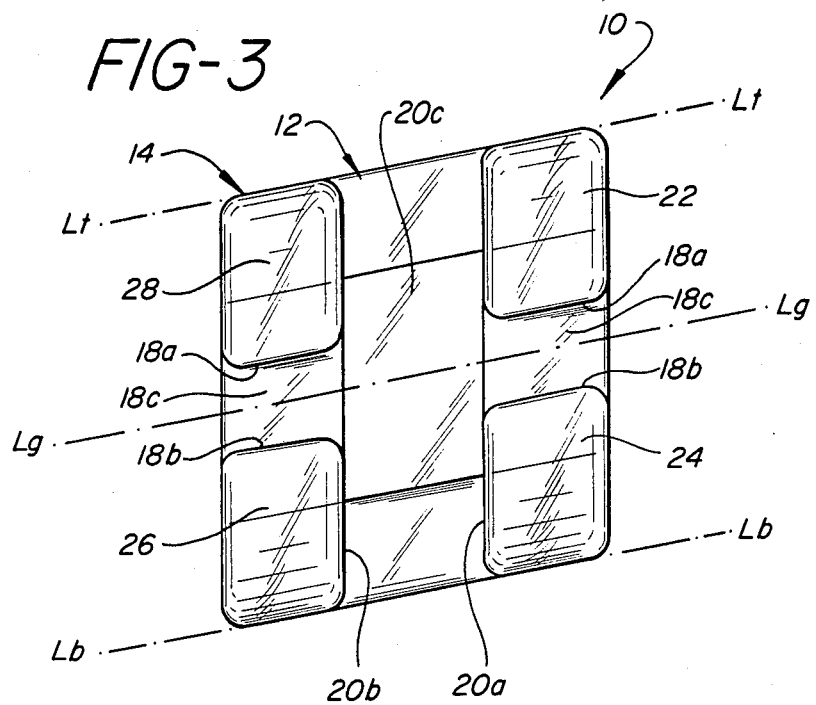
FIG. 3 is a top plan view of the bracket of FIG. 1.
Figure 4:
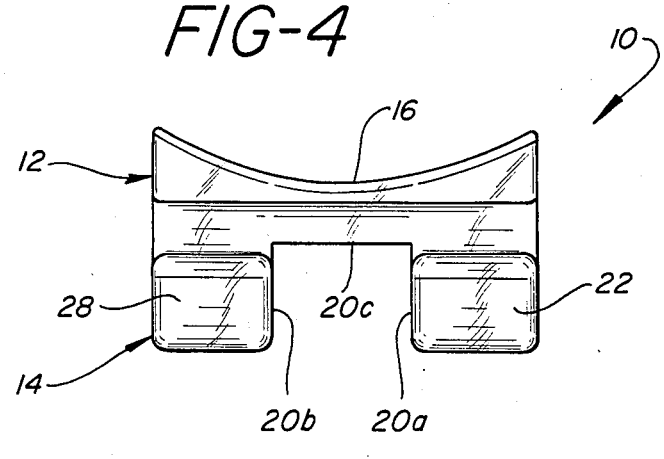
FIG. 4 is a front elevational view of the bracket of FIG. 1.

This invention is directed to the provision of orthodontic brackets made of ion exchange strengthened glass.

As used herein, the term "ion exchange strengthened glass" refers to glass that has been stengthened by a chemothermal ion exchange treatment such that a compressive stress layer is formed on the surface of the glass. Such glasses are known in the art. They are prepared by immersing a glass article in a molten salt bath containing exchangeable ions such that the ions in the molten salt bath will be exchanged for ions in the glass. This treatment is carried out at elevated temperature above the strain point of the glass, but below its deformation temperature. To illustrate a typical process for the ion exchange strengthening of a glass article, an article made of a lithium alumino-silicate glass is immersed in a molten sodium nitrate bath at a temperature of about 400° C. for about four hours. The articles are removed, cooled, and then rinsed in a solvent to remove residual salt. The resulting article is significantly stronger than the original article owing to compressive stresses developed in a thin layer on the surface of the glass.

In carrying out the invention, the orthodontic bracket is first produced in the desired configuration from an ion exchange strengthenable glass, and it is then strengthened by the ion exchange treatment. The brackets may be produced in the desired configuration by the following process:

A glass rod of a predetermined cross-sectional configuration can be produced by known procedures by drawing the rod through a heated graphite die. The glass should be heated to its working temperature, which is usually of the order of 1300° to 1500° C., where its viscosity is of the order of $10^4$ poises. After cooling, the rods may be machined to finish them, cut into individual bracket blanks, and then subjected to the ion exchange treatment. This process will now be explained in more detail with reference to the drawings.

FIGS. 1 through 4 show an orthodontic bracket made in accordance with the invention. The bracket 10 includes a base portion 12 and a body portion 14. The base 12 includes a tooth contacting surface 16 that has a double concavity, as can be seen from FIGS. 2 and 4, to match the contour of the tooth to which the bracket is to be bonded. An archwire groove in the body portion 14 is defined by walls 18a, 18b, 18c. The body portion also contains a "saddle", which is defined by walls 20a, 20b, 20c. The version of bracket shown is a "twin bracket", which contains two pairs of tie wings, shown as 22, 24, 26, and 28.

Figure 12:
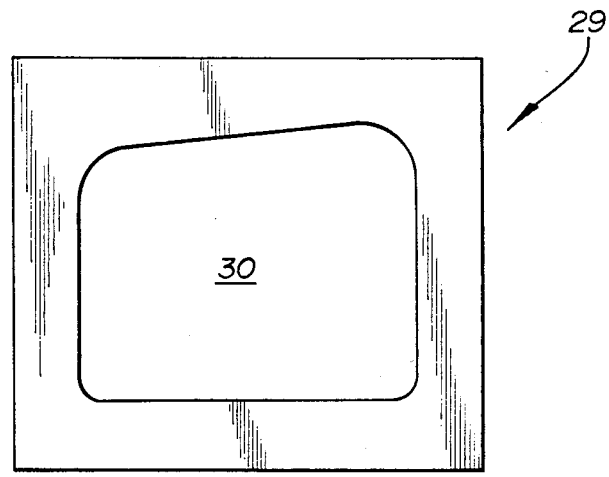
FIG. 12 is plan view of the face of a die that can be used in extruding a glass rod.
Figure 13:
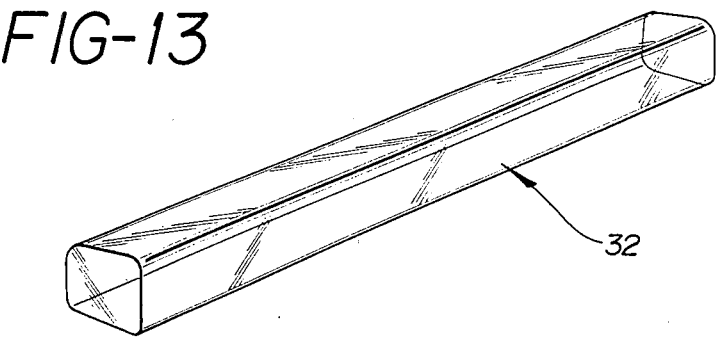
FIG. 13 is a perspective view of a glass rod made by extruding through the die of FIG. 12.

The bracket depicted in FIGS. 1-4 can be produced by the following process:

An ion exchange strengthenable glass is heated to its working temperature and is drawn through a heated graphite die 29 (FIG. 12) having an orifice 30 to produce a rod blank 32 (FIG. 13) having a cross-sectional configuration essentially the same as the configuration of the orifice 30, although reduced in the size. The rod blank 32 is then machined to produce a rod 34 (FIG. 5) from which individual bracket blanks 42 (FIGS. 6 and 7) can be cut, as is explained below.

The rod 34 shown in FIG. 5 includes a longitudinal groove defined by walls 18a, 18b, 18c. The rod 34 also includes a pair of longitudinal grooves 36, 38, cut in either side of the rod 34. All three grooves can be cut in the rod blank 32 by diamond grinding wheels. The rod 34 can then have its bottom side 40 ground to impart concavity. This concavity is most readily seen in FIG. 6 at 15. A second concavity at right angles to the first can then be ground in the bottom of the rod 34 to impart the concavity that is most readily seen in FIG. 4 at 16. Preferably, these two concavities are machined by using a double-contoured grinding wheel in a stepped grinding procedure, which grinds both concavities at once. After the concavities have been ground in the bottom of the rod 34, the saddles can be ground by using a stepped grinding procedure, and then the rod is cut into individual bracket blanks 42. The cuts to make the individual bracket blanks 42 are made at a slight angle, $\alpha$, to a line perpendicular to the longitudinal axis L of the rod 34. This is shown most clearly in FIGS. 6 and 7.

The brackets are then preferably polished to remove minute surface imperfections and to smooth off the contours. A suitable polishing bath is a solution of three parts of 50% aqueous hydroflouric acid and one part of concentrated sulfuric acid. The brackets are immersed in the polishing bath at room temperature for a short time, e. g., one to three minutes, removed, and rinsed. They are then ready for the ion exchange strengthening step.

The brackets are subjected to the ion exchange reaction for a period of time sufficient to strengthen them to a point where they are suitable for use as orthodontic brackets. When the glass used in the brackets is a lithium alumino-silicate, the ion exchange bath can be, for example, molten sodium nitrate, potassium nitrate, sodium sulfate, potassium sulfate, and mixtures thereof. The ion exchange treatment is carried out by immersing the brackets in a bath of molten salt at elevated temperature above the strain point and below the softening point of the glass. To reduce to a minimum the possibility of deformation of the pieces, it is preferred that the molten salt bath be at a temperature not more than 50° to 100° C. over the strain point of the glass. For instance, a suitable temperature for lithium alumino-silicate glass ion exchanged in molten sodium nitrate is about 400° C. The treatment time varies with such factors as specific nature of the glass and treating salt, temperature, and the like, but will usually be from about 2 hours to about 24 hours. A treatment time of from about 3½ to about 4½ hours is suitable for the specific materials discussed above when using a sodium nitrate treating salt. The treatment process is self-limiting in that when all the exchangeable ions at or near the surface of the glass have been exchanged, the ion exchange stops.

After the ion exchange treatment, the brackets are removed from the ion exchange bath, cooled, and then washed clean of excess salt, as by using a bath of acetone, water, or other solvent for the salt. Ultra-sonic treatment may be used to enhance or accelerate the removal of excess salt.

In the Examples, below, the ion exchangeable glass used had the following analysis, by spectroscopy:

| Metal Oxide | % By Weight |
| --- | --- |
| $SiO_2$ | 66.2% |
| $Al_2O_3$ | 21.4 |
| $TiO_2$ | 1.73 |
| $Fe_2O_3$ | 0.06 |
| MgO | 0.01 |
| CaO | 3.44 |
| $Na_2O$ | 0.50 |
| $K_2O$ | 0.30 |
| $SnO_2$ | 1.78 |
| $Li_2O$ | 3.86 |
| $B_2O_3$ | 0.16 |
| $Sb_2O_3$ | 0.35 |
| TOTAL | 99.8% |

EXAMPLES

A large block of ion exchangeable glass was machined into 1.25"×0.125"×0.062: flexural strength bars, and into 0.082"×0.060"×0.150" pieces. The latter pieces had a slot 0.020"×0.030" in cross section machined down the center of the pieces. These latter pieces were made to subject them to a torque test to simulate forces that would be imposed on an installed bracket by an archwire. All the flexural bars and torque test pieces were polished by immersion in a bath of three parts 50% aqueous hydrofluoric acid and one part concentrated (85%) sulfuric acid for two minutes at room temperature. The pieces were removed from the bath and rinsed in water. Half of the pieces were maintained as controls, and the other half were immersed in a molten bath of sodium nitrate at 400° C. for 4 hours. The ion exchanged pieces were removed from the sodium nitrate, cooled, and rinsed in acetone.

The flexural bars were tested using three point loading in an Instron tester. Twenty bars of each condition, as-polished and ion exchanged, were tested. The crosshead speed was 0.01 cm/sec across a one-inch span.

The results of the flexural strength testing are reported in terms of probability of survival at varying flexural strengths (in pounds per square inch—PSI), using Weibull statistical analysis. This type of statistical analysis is explained in "Mechanical Behavior of Ceramics", by R. W. Davidge, pages 133 et seq. Cambridge Univ. Press (1979). Briefly, the analytical procedure is the following:

The strength values for the individual samples are arranged in ascending order. The nth ranked sample from a total of N samples has a probability of survival (of the strength value found for the nth ranked sample) of n/(N+1)×100, in which n represents the ranking, with "1" being the rank of the weakest sample, and "N" being the total number of samples. The results are presented in FIG. 9, which is a graph of flexural strength (x-axis) versus the probability of survival, in per cent (y-axis). A brief summary of the results is also displayed in Table I:

TABLE I

| FLEXURAL TEST - SURVIVAL PROBABILITY | | | |
| --- | --- | --- | --- |
|  | 90% | 50% | 10% |
| As-polished | 17,700 | 27,400 | 37,000 |
| Ion exchanged | 61,500 | 77,200 | 93,000 |

Figure 10:
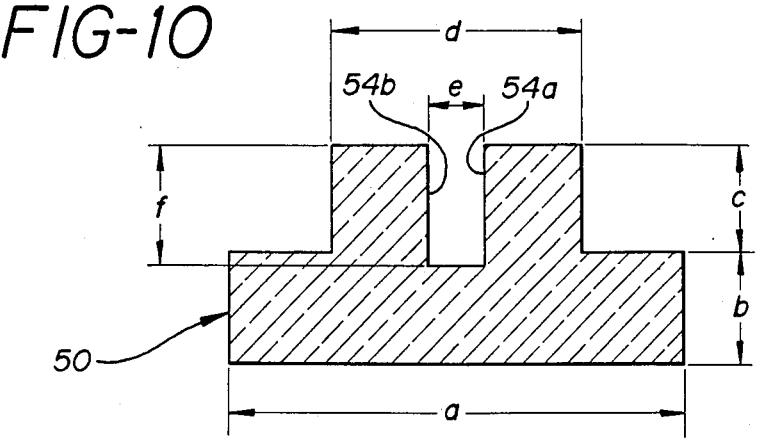
FIG. 10 is a cross-sectional elevation of the test samples used for the torque strength test.

FIG. 10 is a cross-sectional elevation of the torque strength test pieces 50. The specific dimensions of these test pieces were the following:
 a—0.150 inch
 b—0.030 inch
 c—0.030 inch
 d—0.082 inch
 e—0.020 inch
 f—0.032 inch The test pieces were 0.060 inch deep (i.e., in the dimension perpendicular to the plane of the cross-section shown in FIG. 10).

Figure 8:
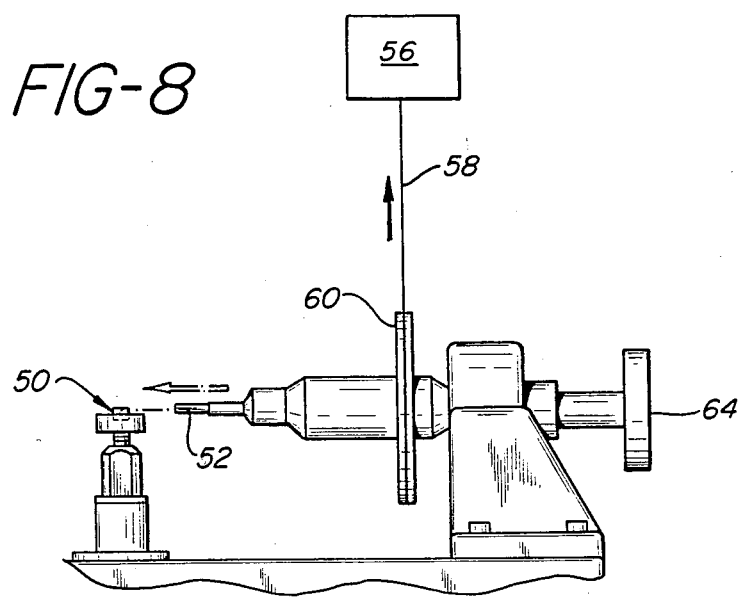
FIG. 8 is a schematic representation of the torque strength test set up.
Figure 8A:
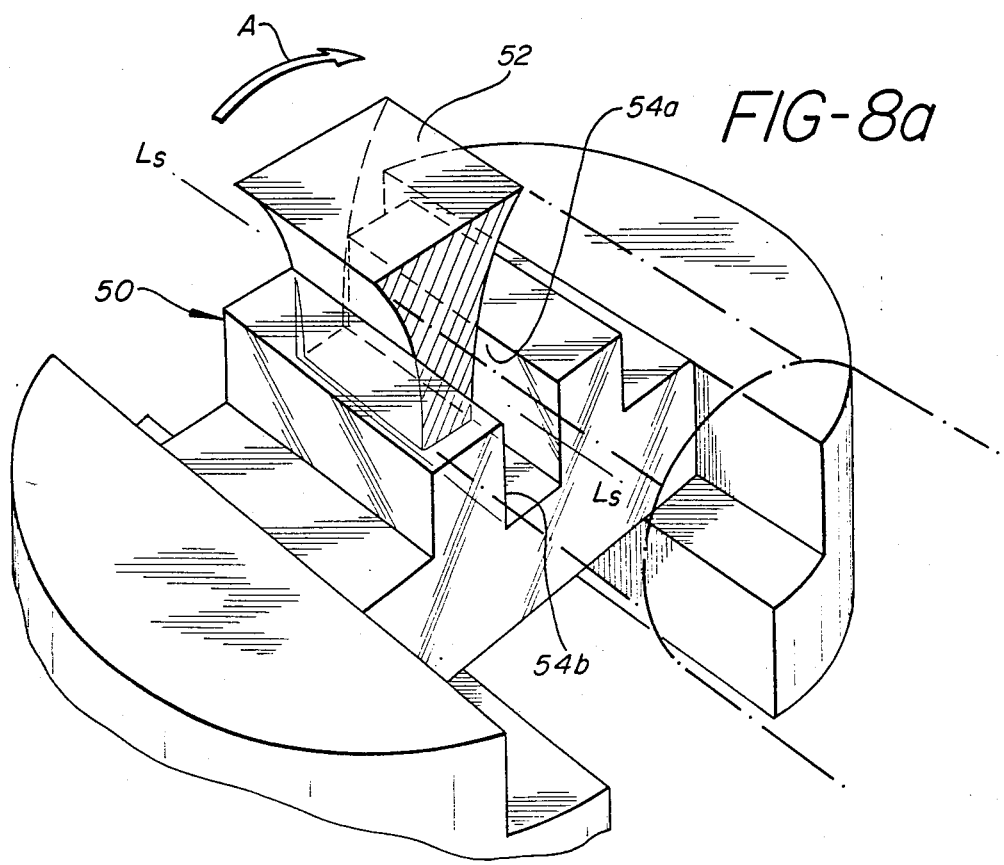
FIG. 8a is an enlarged prespective view of the torque strength test piece mounted in the test set up, showing the movement of the test blade in the slot.

The torque test was carried out as follows:

Referring to FIGS. 8 and 8a, the torque strength test piece 50 is fastened in the test stand with the slot facing upwards and with the longitudinal axis $L_s$ of the slot aligned with the test blade 52. The test blade 52 is inserted in the slot using a positioning wheel 64 to position the blade 52. The test blade 52 is sized to fit snugly in the slot without exerting any expansion force on the walls 54a, 54b, of the slot (refer to FIG. 10). The blade is operatively connected to a load cell 56 via a wire 58 attached to a torque pulley 60. The load cell 56 is operatively connected to an Instron tester (not shown). A rotational force is applied to the test blade 52 by the wire 58 acting on a torque pulley 60. Upon application of a force by the wire 58, the test blade 52 is twisted in the direction of the arrow A shown in FIG. 8a. The test is continued until the test piece 50 breaks. Prior to testing, the Instron is calibrated with a 2000 gram load cell using a 250-gram calibration weight. In applying the load, the torquing device (i.e., the wire 58) moves at a rate of 2 centimeters per minute. (The torque pulley 60 had a diameter of 7.62 centimeters.)

The torque applied by the torque test simulates stresses normally encountered during the latter stages of treatment, when an archwire of rectangular cross-section is often used to impart a torque to the bracket.

It will be noted that the test piece used in the torque test simulates a "single wing" bracket that has only one pair of tie wings, and that the prior description of the preferred embodiment of the brackets of the invention was of "twin brackets" that have two sets of tie wings with an open space ("saddle") between the two sets of tie wings. Therefore, the test piece apparently has more material with which to resist the torque because there is no cut out area or saddle that interrupts the continuity of the side walls of the archwire groove. It is believed that this makes no significant difference in the test results because failure in glasses and ceramics occurs it stresses much lower than the theoretical strength, owing to the presence of minute flaws in the glass.

Figure 11:
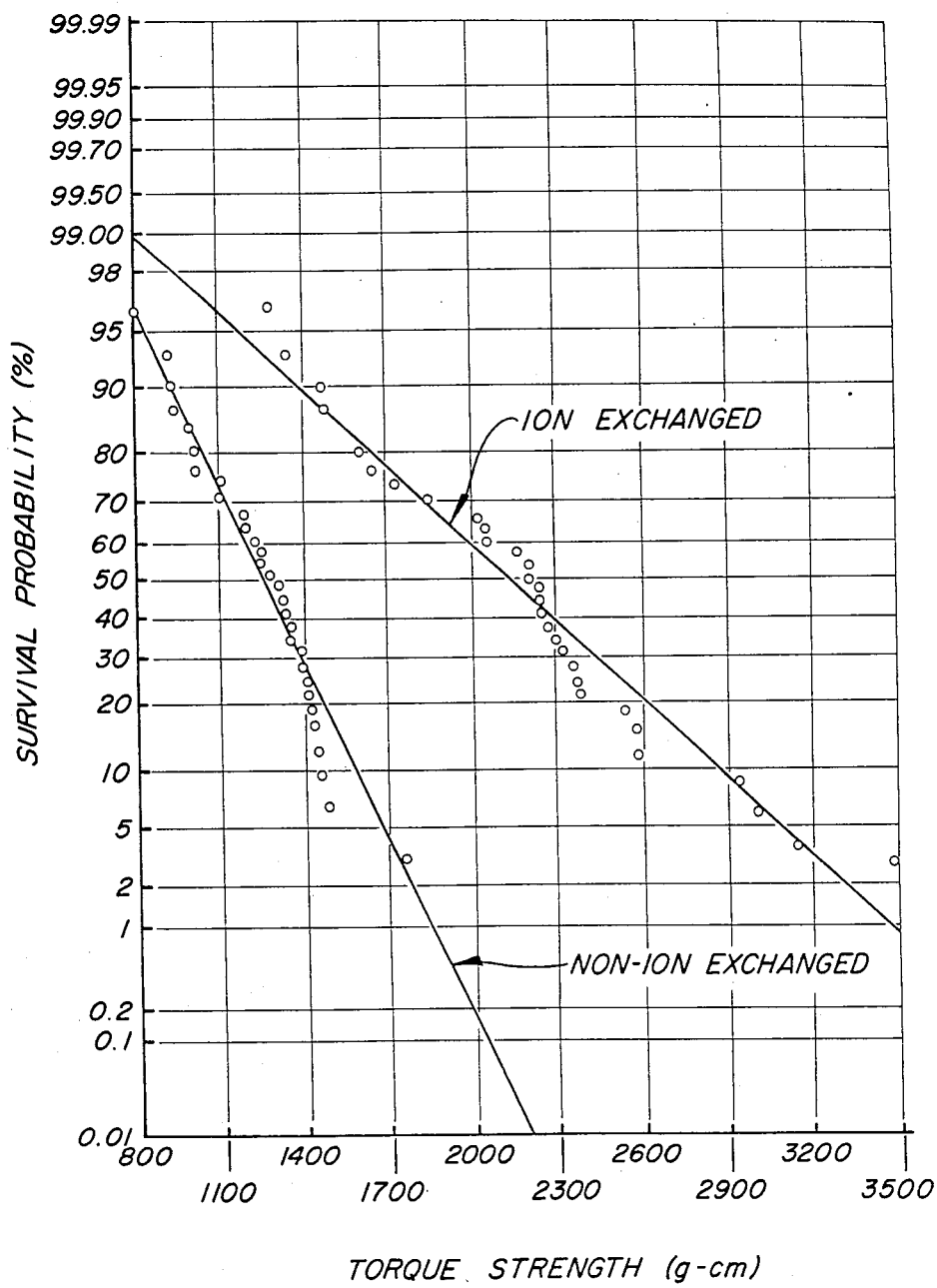
FIG. 11 is a graph of Survival Probability vs. torque strength for glass control and ion exchanged glass torque test pieces.

The results of this test are presented in FIG. 11 in a graph of survival probability, in per cent, versus torque strength in gram-centimeters.

Thirty samples of each were tested. The acid-etched and ion exchange strengthened samples had torque strength values varying from 1276 gm-cm to 3505 gm-cm, and the acid-etched, non-ion exchange strengthened samples had torque strengths varying from 800 to 1783 gm-cm. A brief summary of the results is also displayed in Table II;

TABLE II

| TORQUE STRENGTH - SURVIVAL PROBABILITY | | | |
|---|---|---|---|
| | 90% | 50% | 10% |
| As-polished | 900 | 1250 | 1600 |
| Ion Exchanged | 1400 | 2150 | 2900 |

It is desired that the ion exchange strengthened glass brackets of the invention have a torque strength of at least about 1000 gram-centimeters, measured by the test described above, since 1000 gm-cm of torque is the approximate point at which the strongest archwires in use today yield. As the experimental data presented above indicates, the brackets of the invention have a probability of survival, using Weibull statistical analysis, at 1000 gram-centimeters of torque, of greater than 95 per cent.

What is claimed is:

1. An orthodontic bracket including a base member having a tooth contacting surface, and a body member including walls defining an archwire groove, said bracket comprising ion exchange strengthened glass.

2. The bracket of claim 1 wherein said bracket has a torque strength such that it has at least a 95 per cent probability, by Weibull statistical analysis, of surviving a torque force in the archwire groove of 1000 gram-centimeters.

3. The bracket of claim 1 wherein the glass is a lithium alumino silicate glass strengthened with sodium ions.

4. The bracket of claim 2 wherein the glass is a lithium alumino silicate glass strengthened with sodium ions.

* * * * *